(12) United States Patent
Backes

(10) Patent No.: US 7,303,098 B2
(45) Date of Patent: Dec. 4, 2007

(54) VALVE FOR THE APPLICATION OF DROPS

(75) Inventor: Claus-H. Backes, Saarbruecken (DE)

(73) Assignee: Gaplast GmbH, Altenau (DE)

( * ) Notice: Subject to any disclaimer, the term of this patent is extended or adjusted under 35 U.S.C. 154(b) by 221 days.

(21) Appl. No.: 10/501,204

(22) PCT Filed: Jan. 8, 2003

(86) PCT No.: PCT/EP03/00111

§ 371 (c)(1),
(2), (4) Date: Mar. 9, 2005

(87) PCT Pub. No.: WO03/057587

PCT Pub. Date: Jul. 17, 2003

(65) Prior Publication Data

US 2005/0173456 A1 Aug. 11, 2005

(30) Foreign Application Priority Data

Jan. 9, 2002 (DE) ................. 102 00 519

(51) Int. Cl.
*B65D 37/00* (2006.01)
(52) U.S. Cl. ..................... 222/212; 222/422
(58) Field of Classification Search .......... 222/212, 222/420–422, 494, 1, 195, 105, 481.1
See application file for complete search history.

(56) References Cited

U.S. PATENT DOCUMENTS

| | | | | |
|---|---|---|---|---|
| 5,154,325 A | * | 10/1992 | Ryder et al. | ........... 222/189.06 |
| 5,310,094 A | | 5/1994 | Martinez et al. | |
| 6,079,449 A | | 6/2000 | Gerber | |
| 6,325,253 B1 | * | 12/2001 | Robinson | .................... 222/212 |

FOREIGN PATENT DOCUMENTS

| | | | | |
|---|---|---|---|---|
| DE | 3818629 A1 | | 12/1989 | |
| DE | 4015480 C2 | | 11/1991 | |
| DE | 4119634 A1 | | 12/1992 | |
| DE | 69211648 T2 | | 2/1997 | |
| DE | 69213248 T2 | | 4/1997 | |
| EP | 0602019 A2 | | 6/1994 | |
| EP | 1078864 | * | 2/2001 | ................. 222/212 |
| EP | 0850853 B1 | | 5/2001 | |
| JP | 11240553 A | | 9/1999 | |
| WO | WO 99/55594 A1 | | 11/1999 | |
| WO | WO 00/20293 A1 | | 4/2000 | |
| WO | WO 01/00498 A1 | | 1/2001 | |
| WO | WO 01/76965 | * | 4/2001 | ............ 222/189.06 |

* cited by examiner

*Primary Examiner*—Lien M. Ngo
(74) *Attorney, Agent, or Firm*—Townsend and Townsend and Crew, LLP

(57) ABSTRACT

A valve (20) comprises a housing body (22) with a discharge channel (34), whereby an elastically-deformable membrane (24) is provided in the housing body which seals off the discharge channel. The membrane is sealed at the front end thereof and is arched to form a dome.

17 Claims, 3 Drawing Sheets

VALVE FOR THE APPLICATION OF DROPS

BACKGROUND OF THE INVENTION

The invention relates to a valve for the application of liquid health care products or of health care products dissolved in liquids, in particular of eye drops.

Dropper systems for drop application are known as components of medication packagings in a variety of embodiments. It is disadvantageous with the hitherto known dropper systems that, after a first use, contamination of the liquid to be applied cannot be effectively prevented since, when the screw cap has been removed, germs can enter into the health care product supply through the discharge passage. For this reason, preservatives have hitherto been added to the health care product which are intended to prevent the contamination of the health care product over a limited discharge period. Such preservatives can, however, cause allergic reactions in the user such that it is desirable to omit such additives.

SUMMARY OF THE INVENTION

It is an object of the present invention to provide a simple valve for the application of a health care product which also effectively prevents contamination of the liquid medication after a first use.

The possibility is provided with the valve in accordance with the invention to discharge the liquid to be applied through a sealed passage. The valve in accordance with the invention simultaneously consists of only two functional components, namely the take-up body and the membrane.

To prevent the access of micro-organisms into the medication supply, the discharge passage, and also an optional aeration passage, can be closed impermeable to germs with the help of the elastically deformable membrane. The discharge passage is only opened by the membrane at the moment of the product removal and the discharge passage is closed impermeable to germs again subsequent to the product removal.

In the event that the product quantity propelled out on the removal should be replaced by ambient air in order to avoid underpressure in the container, this air can be subsequently guided in through an aeration passage likewise closed by the elastic membrane. In this process, contamination of the container content is particularly effectively prevented if a sterile filter is provided in front of the orifice of the aeration passage in the take-up body so that the ambient air must first pass through the sterile filter before it can subsequently flow into the container.

In accordance with an advantageous embodiment, the front end of the membrane projects out of the take-up body such that the front end of the membrane can be used simultaneously as an elastic, and thus soft, application tip.

It is also advantageous for the membrane to be closed and/or arched in dome-shape at its front end. In this manner, a drop release is promoted and injuries in the region of the application area, in particular eye injuries, are precluded.

In accordance with a further advantageous embodiment, the membrane and the take-up body contact one another in a sealing manner along a contact section, with the contact section in particular being able to be made as a paraboloid of revolution. Such a shape has proved to be advantageous with respect to a safe opening and closing in the region of the contact section.

The membrane is preferably made as a hollow element open at one end such that good elasticity and thus good closing and sealing properties are ensured with a low material effort.

In accordance with a further advantageous embodiment, the membrane is rotationally symmetrical, and a support element which pre-stresses the membrane in the axial direction is arranged in the interior of the membrane. Such a support element can contribute to sealingly pressing the membrane against the contact section of the take-up body, with a release of the membrane from the take-up body nevertheless taking place against the pre-stressing force on application of the discharge pressure.

An embodiment which can be manufactured particularly easily and so cost-favorably is provided when the valve only consists of three functional components, namely the take-up body, the membrane and the support element. The only components which are still required, apart from the container, are a covering cap and an optional sterile filter. These components are, however, not components of the valve necessary for the function.

In a further advantageous embodiment of the invention, a plurality of ring passages are provided in the valve and communicate with one another via overflow passages. For example, a first ring passage can be provided between the support element and the membrane, and a second ring passage can be provided between the take-up body and the membrane, with the ring passages communicating with one another via an overflow passage in the membrane. In this embodiment, the liquid to be discharged is first transported into a ring space between the support element and the membrane and is subsequently transported into a ring space between the membrane and the take-up body. When the discharge pressure is increased, the liquid can then be transported from the second ring passage through the contact section in the direction of an outflow passage at the front end of the membrane or of the take-up body.

A particularly easy assembly of the valve is provided when the support element in the interior of the membrane is in engagement with the membrane via a latching means, for example via a peripheral latching lip. In this manner, the membrane only has to be pulled over the support element and latched, whereby these two components are already joined together. A simple assembly of this component pre-assembled in this manner can take place in that the support element is inserted into the take-up body with the membrane placed on and is secured in the take-up body via a further latching means. A fully functional valve is hereby provided with only two assembly steps.

The support element preferably extends at its rear end over the total internal cross-section of the take-up body, with a throughflow opening being able to be provided for the liquid to be discharged in this region. A secure holding of the support element and of the membrane is ensured in this manner.

The valve in accordance with the invention is also suitable for a container which is elastically deformable at least regionally, for example for a squeezy bottle. However, the possibility generally also exists of using the valve for rigid containers. In this case, the propelling-out pressure must be produced in another manner.

The present invention will be described in the following purely by way of example with reference to an advantageous embodiment and to the enclosed drawings.

DESCRIPTION OF THE PREFERRED EMBODIMENTS

Figure 1:
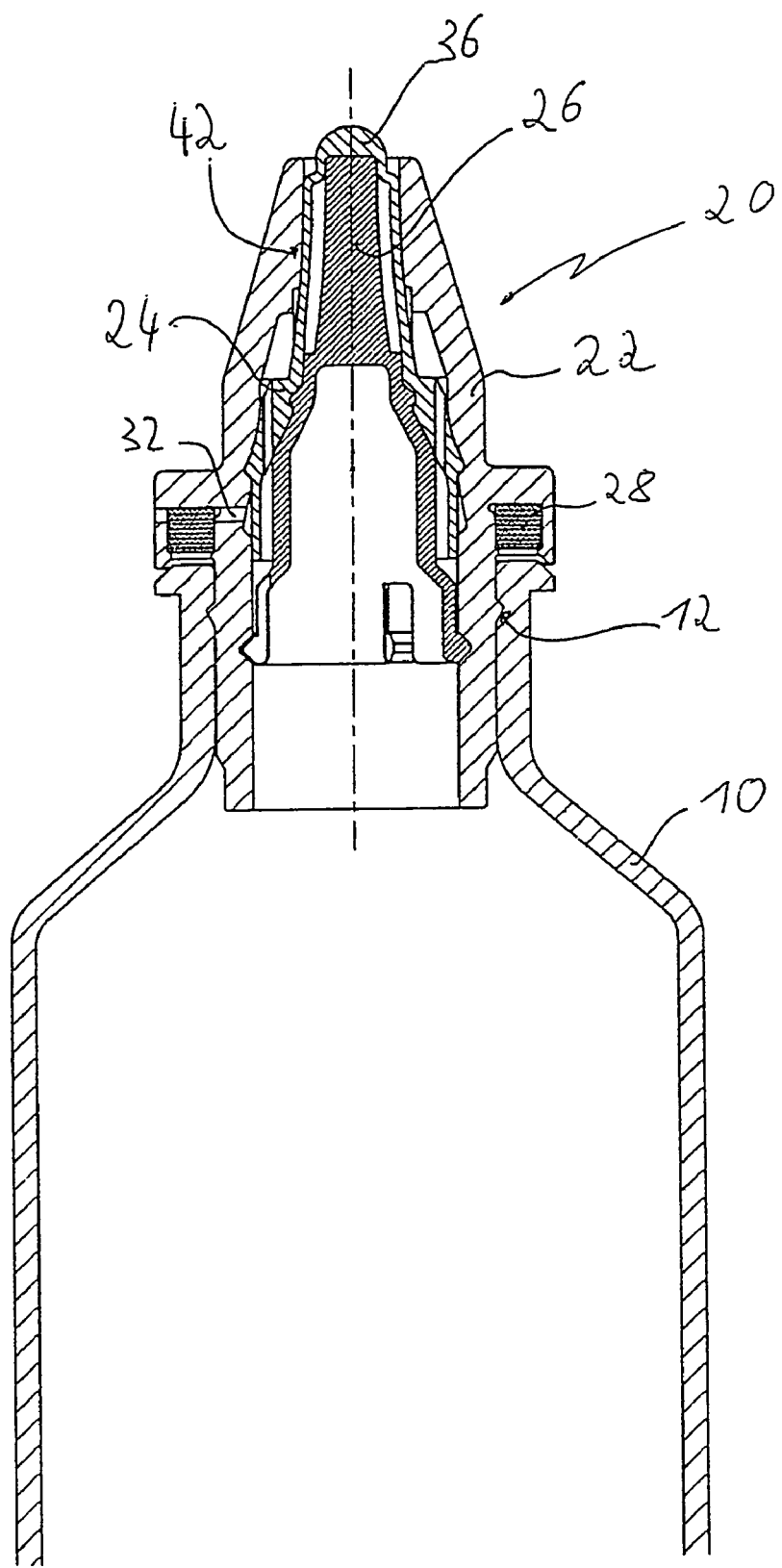
FIG. 1 is a cross-sectional view of a valve secured in a container.

FIG. 1 shows, in cross-section, a container 10 in the form of a squeezy bottle in whose bottle neck a valve 20 is sealingly inserted via a pressing connection 12. The valve 20 consists of three functional components, namely of a take-up body 22, of an elastically deformable membrane 24 and of a support element 26.

Figure 2:
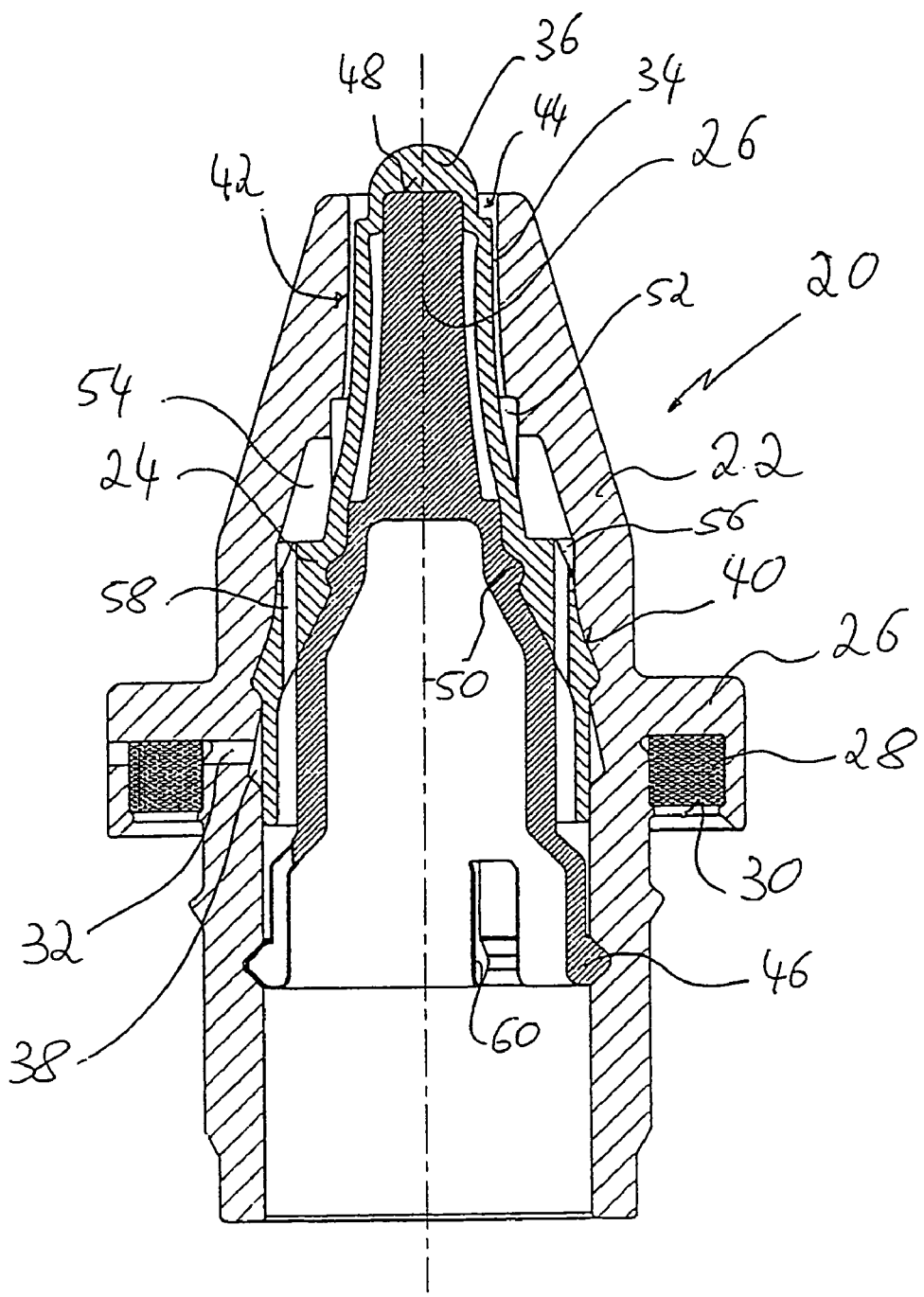
FIG. 2 is an enlarged representation of the valve of FIG. 1 during a product discharge.

FIG. 2 shows an enlarged cross-sectional view of the valve 20. As can be recognized, the take-up body 22 is rotationally symmetrical and consists of a one-piece plastic component which tapers conically in the upper third. A ring-shaped projection 26 is shaped approximately in the middle of the take-up body 22, with a ring-shaped groove, into which a sterile filter 28 has been inserted, being provided in the projection 26. The sterile filter is in communication with the ambient air at its lower end face 30, at the one end. At the other end, the air flowing through the sterile filter 28 can enter into the interior of the intake body 22 via an aeration passage 32. Furthermore, a ring-shaped indentation 38 is provided in the region of the aeration passage 32 at the inner periphery of the take-up body 22.

The take-up body 22 is hollow at its interior and, starting from its lower end, has a hollow cylindrical section which tapers in the upper third in accordance with the outer contour of the take-up body. A discharge passage 34, through which the liquid to be applied can be discharged, is furthermore provided in the region of the front end of the take-up body 22.

The membrane 24 which is inserted into the interior of the take-up body 22 and which is made of an elastomer is a one-piece, rotationally symmetrical component which is elongate, hollow in the interior and closed at its front end. The membrane 24 is arched in a dome-shape to form an approximately semi-spherical dome 36 in the region of the closed front end, with the dome 36 of the membrane 24 projecting out of the take-up body 22.

At its lower end, the membrane 24 is formed in hollow cylindrical manner in the region of the indentation 38 and sealingly covers the indentation 38.

A further indentation 40, into which a complementary formed latching section of the membrane 24 latchingly engages, is provided above the indentation 38 at the inner periphery of the take-up body 22.

In the normal state (cf. FIG. 1), the membrane 24 in the region of the discharge passage 34 sealingly contacts the internal periphery of the take-up body 22 in the region of a contact section 42. In the region of this contact section 42, the inner jacket surface of the discharge passage 34 is designed as a paraboloid of revolution, with the membrane 24 having the same outer contour of a paraboloid of revolution at its outer periphery in this section. A discontinuous transition is provided between the outer contour of a paraboloid of revolution of the membrane 24 and the dome 36 at the upper end of the discharge passage 34 in the region of the dome 36, whereby a discharge passage 44 is formed.

The support body 26, which is likewise a rotationally symmetrical component made in one piece from plastic, is inserted into the interior of the membrane 24. The support element 26 serves, on the one hand, to pre-stress the membrane 24 axially in the region of the contact section 42 and, on the other hand, to hold the membrane in the take-up body 22. For this purpose, the support element is provided at its lower end with a ring-shaped projection 46 which can be latched into a correspondingly desired ring groove in the interior of the take-up body 22. At its upper end, the support element extends up to and into the base region of the dome 36. It is there received in a hollow cylindrical recess 48 at the inner front end of the membrane 24.

In the region of the contact section 42, the support element 26 is made in pin-shape, with the outer contour of the pin-shaped section likewise being made as a paraboloid of revolution. However, as the Figures show, there is a clear spacing between the outer jacket surface of the pin-shaped section of the pin element 26 and the inner peripheral area of the membrane 24 in this section which makes it possible for the membrane to deform inwardly in the direction of the support element 26 (cf. FIG. 2).

The support element 26 is provided approximately at the middle at its outer periphery with a peripheral latching lip 50 which latchingly engages into a complementary formed, ring-shaped latching recess at the inner periphery of the membrane 24. The membrane is hereby lightly tensioned axially between the base of the dome 36 and the latching lip 50.

As FIG. 1 shows, the membrane 24 with the support element 26 is inserted into the take-up body 22 such that, when the support element 26 is latched and when the membrane 24 is latched, the membrane contacts the inner periphery of the take-up body areally and. sealingly along the contact section 42. A ring passage 52 (FIG. 2), which is preceded by at least one axial overflow passage 54, is formed in the take-up body 22 at the inner orifice of the contact section 42, the overflow passage in turn being preceded by a further ring passage 56. Both the ring passage 52 as well as the overflow passage 54 and the ring passage 56 are bounded at the outer periphery by the take-up body 22 and at the inner periphery by the membrane 24.

As in particular FIG. 2 shows, a plurality of axial overflow passages 58 are provided in the membrane 24 and connect the interior of the membrane 24 to the outer side of the membrane. Liquid can hereby flow from the interior of the take-up body 22 into the ring passage 56.

The support element 26 furthermore has a plurality of throughflow openings 60 at its lower side which are distributed over the periphery of the support element 26 and which extend in the axial direction.

Figure 3:
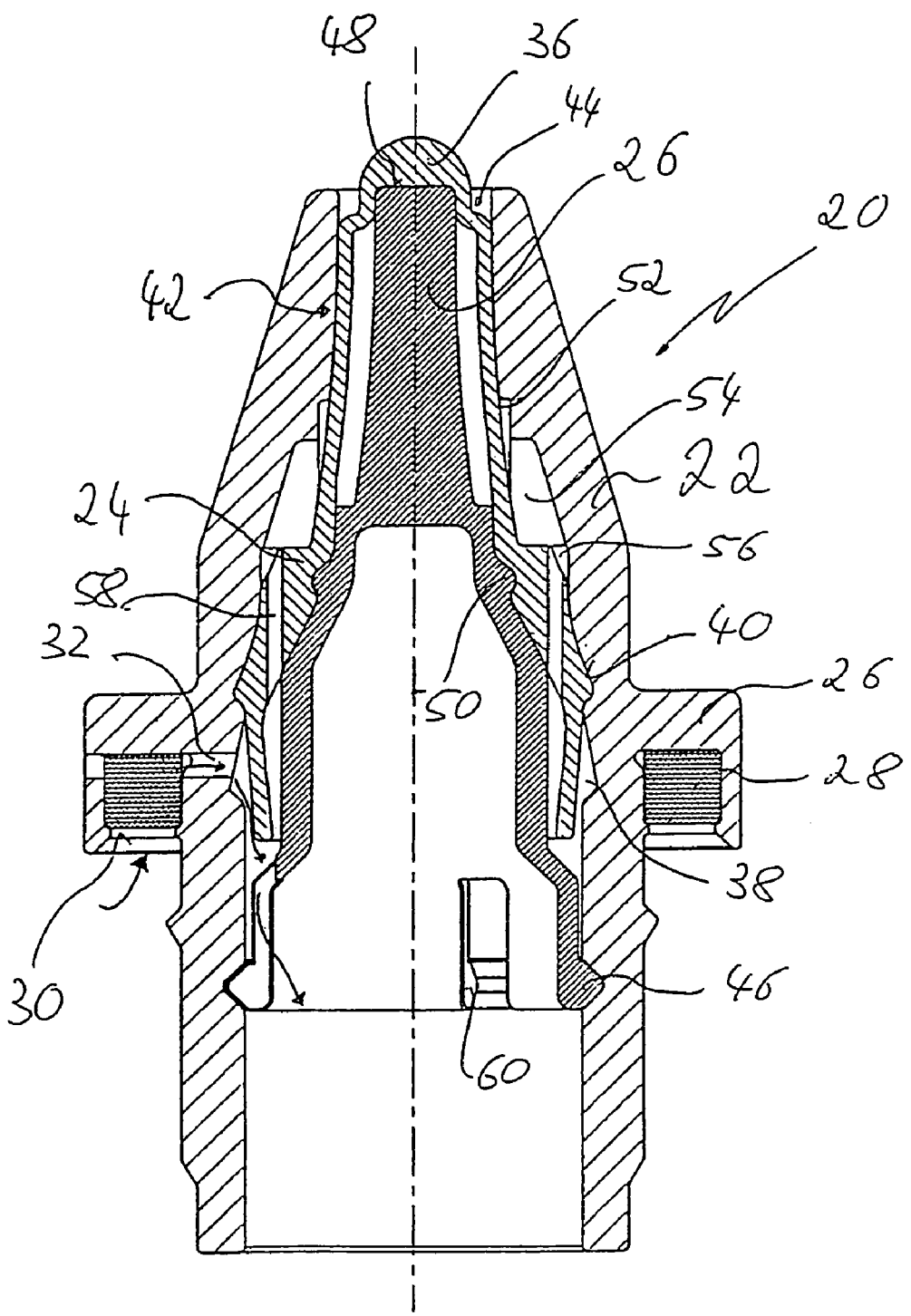
FIG. 3 shows the valve of FIG. 2 during the pressure compensation.

The function of the valve shown in FIGS. 1 to 3 is as follows:

In the state of rest, the membrane 24 of the valve 20 is in the position shown in FIG. 1 in which the membrane 24 closes both the discharge passage 34 (FIG. 2) and the aeration passage 32 in an outwardly sealed manner such that no liquid can flow out of the interior of the container 10 and no contaminated air can penetrate into the interior of the container 10.

A desired discharge pressure is applied for the discharge of liquid from the container 10, for example by squeezing the at least regionally elastically deformable container 10. Overpressure is hereby produced in the interior of the container 10 which propels out the liquid located in the container 10 through the discharge passage 34 (cf. FIG. 2). In this process, the liquid initially flows into the interior of the take-up body 22, from there through the throughflow openings 60 into the interior of the membrane 24 and from there through the overflow passages 58 into the ring passage 56. From there, the liquid enters into the ring passage 52 through the overflow passage 54, with the pressure exerted on the membrane 24 by the liquid raising the membrane from the take-up body 22 inwardly in the direction of the support element 26 such that a ring gap, as is shown in FIG. 2, is created between the membrane 24 and the take-up body 22. Subsequently, the liquid enters into the outflow passage 44 and collects as drops at the dome 36 such that an application of the drop is possible, for example in the eye of a user.

FIG. 3 shows the state of the membrane 24 after the discharge pressure has been reduced. The overpressure in the interior of the container 10 is hereby reduced and the restoring forces of the pre-stressed elastic membrane 24 have the effect that it again firmly contacts the inner jacket surface of the contact region 42 of the take-up body 22 such that the discharge passage 34 is again sealingly closed.

The underpressure created in the container 10, which is produced by the discharge of the liquid, subsequently has the effect that the lower marginal region of the membrane 24, which has previously sealingly closed the aeration passage 32 or the indentation 38, rises from the inner periphery of the intake body 22, as is represented in FIG. 3. Ambient air can hereby subsequently flow into the interior of the container 10 via the sterile filter 28 and the aeration passage 32 and the indentation 38 until pressure compensation has been achieved between the ambient pressure and the internal container pressure. The corresponding air flow is indicated by arrows in FIG. 3.

If the valve is used in a dropper system which does not require any pressure compensation, the aeration passage 32 and the sterile filter 28 can be omitted.

The invention claimed is:

1. A valve for the drop application of a liquid stored in a container comprising a take-up body which has a discharge passage for the liquid, and a single elastically deformable membrane which is closed at its front end arranged in the take-up body and sealingly closing the discharge passage, the take-up body having an aeration passage extending through the take-up body for a follow-up air flow, the membrane also sealingly closing the aeration passage.

2. A valve in accordance with claim 1, wherein the front end of the membrane has an arched in dome-shape.

3. A valve in accordance with claim 1, wherein the front end of the membrane projects out of the take-up body.

4. A valve in accordance with claim 1, wherein the membrane is made as a hollow body open at one end.

5. A valve in accordance with claim 1, including a support element which pre-stresses the membrane in the axial direction and is arranged in an interior of the membrane.

6. A valve in accordance with claim 1, including a support element provided in the interior of the membrane and which is in engagement with the membrane via at least one latching means.

7. A valve in accordance with claim 1, including a support element which is provided for the membrane is in engagement with the take-up body via at least one latching means.

8. A valve in accordance with claim 1, including a support body provided for the membrane and extending from beneath an aeration passage in the take-up body up to and into a region of the upper end of the membrane.

9. A valve in accordance with claim 1, including a support body 6 for the membrane and extending over a total inner cross-section of the take-up body at its lower end and having at least one throughflow opening in a vicinity of the lower end.

10. A valve in accordance with claim 1, including a support body and wherein a ring passage is provided between the support body and the membrane.

11. A valve in accordance with claim 1, wherein the take-up body and the membrane define a ring passage between them.

12. A valve in accordance with claim 10, including first and second ring passages between the take-up body and the membrane; and at least one overflow passage in the membrane connecting the first and second ring passages to one another.

13. A valve in accordance with claim 1, wherein the membrane and the take-up body sealingly contact one another along a contact section configured as a paraboloid of revolution.

14. A valve in accordance with claim 13, wherein a ring passage is provided at a start of the contact section and an outflow passage is provided at an end of the contact section.

15. A valve in accordance with claim 1, including a sterile filter in the take-up body in front of the orifice of the aeration passage.

16. A valve in accordance with claim 1, comprising only three functional components, namely the take-up body, the membrane and a support body.

17. A dropper system comprising a container and a valve in accordance with claim 1.

* * * * *